(12) United States Patent
Fu et al.

(10) Patent No.: US 7,858,351 B2
(45) Date of Patent: Dec. 28, 2010

(54) S-ADENOSYLMETHIONINE SYNTHETASE MUTANTS, THE DNAS ENCODING THE SAME AND USES OF THE MUTANTS

(75) Inventors: Rongzhao Fu, Shatin (HK); Tianzuo Zhang, Shatin (HK); Jun Wang, Shatin (HK)

(73) Assignee: Geneharbor ( Hong Kong) Technologies, Ltd., Hong Kong (CN)

( * ) Notice: Subject to any disclaimer, the term of this patent is extended or adjusted under 35 U.S.C. 154(b) by 0 days.

(21) Appl. No.: 12/438,680

(22) PCT Filed: Aug. 30, 2007

(86) PCT No.: PCT/CN2007/002603

§ 371 (c)(1),
(2), (4) Date: Apr. 14, 2009

(87) PCT Pub. No.: WO2008/034338

PCT Pub. Date: Mar. 27, 2008

(65) Prior Publication Data

US 2009/0203080 A1    Aug. 13, 2009

(30) Foreign Application Priority Data

Aug. 31, 2006    (CN) .................. 2006 1 0127636

(51) Int. Cl.
*C12P 19/40* (2006.01)
*C12N 9/10* (2006.01)
*C12Q 1/48* (2006.01)

(52) U.S. Cl. ............................. 435/193; 435/88; 435/15

(58) Field of Classification Search ........................ None
See application file for complete search history.

(56) References Cited

FOREIGN PATENT DOCUMENTS

| CN | 1379102 A | 11/2002 |
|---|---|---|
| CN | 1483829 A | 3/2004 |
| WO | 2005108561 A2 | 11/2005 |

OTHER PUBLICATIONS

Graham et al JBC 2000, 275, 4055-4059.*
Chica et al. Curr Opin Biotechnol. Aug. 2005;16(4):378-84.*
Seffernick et al. J Bacteriol. Apr. 2001; 183 (8): 2405-10.*
Witkowski et al. Biochemistry. Sep. 7, 1999; 38(36): 11643-50.*
Lee et al.; "Cloning, Sequencing and Biochemical Characterization of Xylose Isomerase from *Thermoanaerobacterium saccharolyticum* Strain B6A-R1"; Journal of General Microbiology; 1993; pp. 1227-1234; vol. 139; Great Britain.
IUPAC-IUB Joint Commission on Biochemical Nomenclature; "Nomenclature and Symbolism for Amino Acids and Peptices"; Eur. J. Biochem.; 1984; pp. 9-37; vol. 138.
Ho et al.; "Site-Directed Mutagenesis by Overlap Extension Using the Polymerase Chain Reaction"; Gene, 1989; pp. 51-59; vol. 77; Elsevier Science Publishers B.V.
White.; "Methods in Molecular Biology 15; PCR Protocol: Current Methods and Applications"; 1993; 8 pages; Humana Press Inc., Totawa, New Jersey.
Chiang et al.; "S-Adenosylmethionine and Methylation"; The FASEB Journal; Mar. 1996; pp. 471-480; vol. 10.
Bottiglieri; "S-Adenosyl-L-Methionine (SAMe): from the Bench to the Bedside-Molecular Basis of a Pleiotrophic Molecule"; American Journal of Clinical Nutrition; 2002; pp. 1151S-1157S; vol. 76; USA.
Mato et al.; "S-Adenosylmethionine Synthesis: Molecular Mechanisms and Clinical Implications"; Pharmacol. Ther.; 1997; pp. 265-280; vol. 73, No. 3; Elsevier Science Inc.
Lu; "Methionine adenosyltransferase and Liver Disease: It's All About SAM"; Gastroenterology; Feb. 1998; pp. 403-407; vol. 114, No. 2.
"S-Adenosylmethionine Synthetase"; *Methanocaldococcus jannaschii* DSM 2661; 3 pages; GenBank Accession No. NP_248203; Dec. 3, 2005.
"*Methanocaldococcus jannaschii* DSM 2661, Complete Genome"; *Methanocaldococcus jannaschii* DSM 2661; 732 pages; GenBank Accession No. NC_000909, Apr. 25, 2009.

* cited by examiner

*Primary Examiner*—Delia M Ramirez
*Assistant Examiner*—Md. Younus Meah
(74) *Attorney, Agent, or Firm*—The Webb Law Firm

(57) ABSTRACT

The invention discloses a series of *Methanococcus jannaschii* S-adenosylmethionine synthetase mutants with improved thermostability and high catalytic activity obtained by using gene mutation technique, characterized in that these mutants refer to an enzyme using Sequence 2 in the Sequence Listing as the reference sequence and contains at least one mutation at position 102, position 93, position 230, and position 357 and has a catalytic activity at least 70% higher than that of the wild-type S-adenosylmethionine synthetase using adenosine triphosphate (ATP) and methionine as substrates. These S-adenosylmethionine synthetase mutants can be used in the production of S-adenosylmethionine.

13 Claims, 2 Drawing Sheets

SEQUENCE LISTING

<160> NUMBER OF SEQ ID NOS: 18

<210> SEQ ID NO 1
<211> LENGTH: 1221
<212> TYPE: DNA
<213> ORGANISM: Methanococcus jannaschii

<400> SEQUENCE: 1

```
atgagaaaca taattgtaaa aaaattagat gttgaaccaa ttgaagaaag accaactgaa        60
attgttgaga ggaagggatt ggggcatcca gattcaattt gtgatggtat tgctgagagt       120
gttagtaggg ctttatgtaa gatgtacatg gagaagtttg gaactatttt gcaccacaat       180
acagaccaag ttgagcttgt aggggacat gcatatccta agtttggagg aggagtaatg        240
gtaagcccta tttatatttt attatctgga agagcaacaa tggaaatctt agataaggag       300
aaaaatgaag ttataaagct cccagtagga acaactgctg ttaaagctgc taaagaatat       360
ttaaagaagg ttttaagaaa tgttgatgtt gataaagatg ttattattga ctgcagaatt       420
gggcagggaa gtatggattt agttgatgtc tttgagagac aaaagaatga agttccttta       480
gctaatgata catcatttgg agtaggttat gctccattat caacaacaga gaggttagtt       540
ttagaaacag agagattttt aaatagtgat gagttaaaga atgagattcc agctgtagga       600
gaggacataa aggttatggg attaagagag ggtaagaaga taacttttaac cattgctatg       660
```

-continued

```
gctgttgttg ataggtatgt taaaaatatt gaggaatata aggaagttat tgaaaaggtt      720
agaaagaagg ttgaagattt agctaagaag atagctgatg gatatgaggt tgaaattcat      780
ataaatacag cagatgatta tgagagggag agtgtctatc taacagttac tggaacatca      840
gcagagatgg gggatgatgg ttcagttggg agaggaaata gagttaatgg attgataact      900
ccattcagac ctatgagtat ggaggcagca agtggtaaaa acccagtaaa tcacgttggt      960
aaaatctaca atatcttagc aaacttaata gcaaacgata ttgccaaatt ggaaggagtt     1020
aaagagtgct gtgttagaat atttagccaa attggtaagc caatcaatga gccaaaggct     1080
ttagatatag aaattataac tgaagatagc tatgatataa aggatattga accaaaagca     1140
aaagagatag ccaataaatg gttagataac atcatggaag ttcaaaagat gattgttgaa     1200
ggaaaagtaa ctacattcta a                                               1221
```

<210> SEQ ID NO 2
<211> LENGTH: 406
<212> TYPE: PRT
<213> ORGANISM: Methanococcus jannaschii

<400> SEQUENCE: 2

```
Met Arg Asn Ile Ile Val Lys Lys Leu Asp Val Glu Pro Ile Glu Glu
  1               5                  10                  15

Arg Pro Thr Glu Ile Val Glu Arg Lys Gly Leu Gly His Pro Asp Ser
                 20                  25                  30

Ile Cys Asp Gly Ile Ala Glu Ser Val Ser Arg Ala Leu Cys Lys Met
             35                  40                  45

Tyr Met Glu Lys Phe Gly Thr Ile Leu His His Asn Thr Asp Gln Val
         50                  55                  60

Glu Leu Val Gly Gly His Ala Tyr Pro Lys Phe Gly Gly Gly Val Met
 65                  70                  75                  80

Val Ser Pro Ile Tyr Ile Leu Leu Ser Gly Arg Ala Thr Met Glu Ile
                 85                  90                  95

Leu Asp Lys Glu Lys Asn Glu Val Ile Lys Leu Pro Val Gly Thr Thr
                100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
        130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
    210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
            260                 265                 270
```

```
Tyr Leu Thr Val Thr Gly Thr Ser Ala Glu Met Gly Asp Asp Gly Ser
        275                 280                 285

Val Gly Arg Gly Asn Arg Val Asn Gly Leu Ile Thr Pro Phe Arg Pro
        290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
                340                 345                 350

Lys Pro Ile Asn Glu Pro Lys Ala Leu Asp Ile Glu Ile Ile Thr Glu
                355                 360                 365

Asp Ser Tyr Asp Ile Lys Asp Ile Glu Pro Lys Ala Lys Glu Ile Ala
        370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 3
<211> LENGTH: 406
<212> TYPE: PRT
<213> ORGANISM: Artificial
<220> FEATURE:
<223> OTHER INFORMATION: The Asn residue at position 102 of the parent
      has been changed to Ser.

<400> SEQUENCE: 3

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
                20                  25                  30

Ile Cys Asp Gly Ile Ala Glu Ser Val Ser Arg Ala Leu Cys Lys Met
        35                  40                  45

Tyr Met Glu Lys Phe Gly Thr Ile Leu His His Asn Thr Asp Gln Val
50                  55                  60

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Thr Met Glu Ile
                85                  90                  95

Leu Asp Lys Glu Lys Ser Glu Val Ile Lys Leu Pro Val Gly Thr Thr
                100                 105                 110

Ala Val Lys Ala Ala Lys Glu Tyr Leu Lys Lys Val Leu Arg Asn Val
        115                 120                 125

Asp Val Asp Lys Asp Val Ile Ile Asp Cys Arg Ile Gly Gln Gly Ser
130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
        180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
        210                 215                 220
```

```
Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
                260                 265                 270

Tyr Leu Thr Val Thr Gly Thr Ser Ala Glu Met Gly Asp Asp Gly Ser
                275                 280                 285

Val Gly Arg Gly Asn Arg Val Asn Gly Leu Ile Thr Pro Phe Arg Pro
290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
                340                 345                 350

Lys Pro Ile Asn Glu Pro Lys Ala Leu Asp Ile Glu Ile Thr Glu
                355                 360                 365

Asp Ser Tyr Asp Ile Lys Asp Ile Glu Pro Lys Ala Lys Glu Ile Ala
                370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 4
<211> LENGTH: 406
<212> TYPE: PRT
<213> ORGANISM: Artificial
<220> FEATURE:
<223> OTHER INFORMATION: The Asn residue at position 102 of the parent
      has been changed to Asp.

<400> SEQUENCE: 4

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
                20                  25                  30

Ile Cys Asp Gly Ile Ala Glu Ser Val Ser Arg Ala Leu Cys Lys Met
            35                  40                  45

Tyr Met Glu Lys Phe Gly Thr Ile Leu His His Asn Thr Asp Gln Val
    50                  55                  60

Glu Leu Val Gly Gly His Ala Tyr Pro Lys Phe Gly Gly Val Met
65                  70                  75                  80

Val Ser Pro Ile Tyr Ile Leu Ser Gly Arg Ala Thr Met Glu Ile
                85                  90                  95

Leu Asp Lys Glu Lys Asp Glu Val Ile Lys Leu Pro Val Gly Thr Thr
                100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
```

-continued

```
                165                 170                 175
Glu Arg Leu Val Leu Glu Thr Glu Arg Phe Leu Asn Ser Asp Glu Leu
            180                 185                 190
Lys Asn Glu Ile Pro Ala Val Gly Glu Asp Ile Lys Val Met Gly Leu
        195                 200                 205
Arg Glu Gly Lys Lys Ile Thr Leu Thr Ile Ala Met Ala Val Val Asp
    210                 215                 220
Arg Tyr Val Lys Asn Ile Glu Glu Tyr Lys Glu Val Ile Glu Lys Val
225                 230                 235                 240
Arg Lys Lys Val Glu Asp Leu Ala Lys Lys Ile Ala Asp Gly Tyr Glu
                245                 250                 255
Val Glu Ile His Ile Asn Thr Ala Asp Asp Tyr Glu Arg Glu Ser Val
            260                 265                 270
Tyr Leu Thr Val Thr Gly Thr Ser Ala Glu Met Gly Asp Asp Gly Ser
        275                 280                 285
Val Gly Arg Gly Asn Arg Val Asn Gly Leu Ile Thr Pro Phe Arg Pro
    290                 295                 300
Met Ser Met Glu Ala Ala Ser Gly Lys Asn Pro Val Asn His Val Gly
305                 310                 315                 320
Lys Ile Tyr Asn Ile Leu Ala Asn Leu Ile Ala Asn Asp Ile Ala Lys
                325                 330                 335
Leu Glu Gly Val Lys Glu Cys Cys Val Arg Ile Phe Ser Gln Ile Gly
            340                 345                 350
Lys Pro Ile Asn Glu Pro Lys Ala Leu Asp Ile Glu Ile Thr Glu
        355                 360                 365
Asp Ser Tyr Asp Ile Lys Asp Ile Glu Pro Lys Ala Lys Glu Ile Ala
    370                 375                 380
Asn Lys Trp Leu Asp Asn Ile Met Glu Val Gln Lys Met Ile Val Glu
385                 390                 395                 400
Gly Lys Val Thr Thr Phe
                405

<210> SEQ ID NO 5
<211> LENGTH: 406
<212> TYPE: PRT
<213> ORGANISM: Artificial
<220> FEATURE:
<223> OTHER INFORMATION: The Asn residue at position 102 of the parent
      has been changed to His.

<400> SEQUENCE: 5

Met Arg Asn Ile Ile Val Lys Lys Leu Asp Val Glu Pro Ile Glu Glu
1               5                   10                  15
Arg Pro Thr Glu Ile Val Glu Arg Lys Gly Leu Gly His Pro Asp Ser
            20                  25                  30
Ile Cys Asp Gly Ile Ala Glu Ser Val Ser Arg Ala Leu Cys Lys Met
        35                  40                  45
Tyr Met Glu Lys Phe Gly Thr Ile Leu His His Asn Thr Asp Gln Val
    50                  55                  60
Glu Leu Val Gly Gly His Ala Tyr Pro Lys Phe Gly Gly Val Met
65                  70                  75                  80
Val Ser Pro Ile Tyr Ile Leu Leu Ser Gly Arg Ala Thr Met Glu Ile
                85                  90                  95
Leu Asp Lys Glu Lys His Glu Val Ile Lys Leu Pro Val Gly Thr Thr
            100                 105                 110
```

```
Ala Val Lys Ala Ala Lys Glu Tyr Leu Lys Val Leu Arg Asn Val
        115                 120                 125

Asp Val Asp Lys Asp Val Ile Ile Asp Cys Arg Ile Gly Gln Gly Ser
130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
    210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
        275                 280                 285

Val Gly Arg Gly Asn Arg Val Asn Gly Leu Ile Thr Pro Phe Arg Pro
    290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
            340                 345                 350

Lys Pro Ile Asn Glu Pro Lys Ala Leu Asp Ile Glu Ile Ile Thr Glu
        355                 360                 365

Asp Ser Tyr Asp Ile Lys Asp Ile Glu Pro Lys Ala Lys Glu Ile Ala
    370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 6
<211> LENGTH: 406
<212> TYPE: PRT
<213> ORGANISM: Artificial
<220> FEATURE:
<223> OTHER INFORMATION: The Asn residue at position 102 of the parent
      has been changed to Ile.

<400> SEQUENCE: 6

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
                20                  25                  30

Ile Cys Asp Gly Ile Ala Glu Ser Val Ser Arg Ala Leu Cys Lys Met
            35                  40                  45

Tyr Met Glu Lys Phe Gly Thr Ile Leu His His Asn Thr Asp Gln Val
        50                  55                  60
```

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Thr Met Glu Ile
            85                  90                  95

Leu Asp Lys Glu Lys Ile Glu Val Ile Lys Leu Pro Val Gly Thr Thr
            100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
            165                 170                 175

Glu Arg Leu Val Leu Glu Thr Gly Arg Phe Leu Asn Ser Asp Glu Leu
            180                 185                 190

Lys Asn Glu Ile Pro Ala Val Gly Glu Asp Ile Lys Val Met Gly Leu
            195                 200                 205

Arg Glu Gly Lys Lys Ile Thr Leu Thr Ile Ala Met Ala Val Val Asp
210                 215                 220

Arg Tyr Val Lys Asn Ile Glu Gly Tyr Lys Glu Val Ile Glu Lys Val
225                 230                 235                 240

Arg Lys Lys Val Glu Asp Leu Ala Lys Lys Ile Ala Asp Gly Tyr Glu
            245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
            275                 280                 285

Val Gly Arg Gly Asn Arg Val Asn Gly Leu Ile Thr Pro Phe Arg Pro
290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
            325                 330                 335

Leu Glu Gly Val Lys Glu Cys Cys Val Arg Ile Phe Ser Gln Ile Gly
            340                 345                 350

Lys Pro Ile Asn Glu Pro Lys Ala Leu Asp Ile Glu Ile Thr Glu
            355                 360                 365

Asp Ser Tyr Asp Ile Lys Asp Ile Glu Pro Lys Ala Lys Glu Ile Ala
370                 375                 380

Asn Lys Trp Leu Asp Asn Ile Met Glu Val Gln Lys Met Ile Val Glu
385                 390                 395                 400

Gly Lys Val Thr Thr Phe
            405

<210> SEQ ID NO 7
<211> LENGTH: 406
<212> TYPE: PRT
<213> ORGANISM: Artificial
<220> FEATURE:
<223> OTHER INFORMATION: The Asn residue at position 102 of the parent
      has been changed to Pro.

<400> SEQUENCE: 7

Met Arg Asn Ile Ile Val Lys Lys Leu Asp Val Glu Pro Ile Glu Glu

-continued

```
1               5                   10                  15
Arg Pro Thr Glu Ile Val Glu Arg Lys Gly Leu Gly His Pro Asp Ser
                20                  25                  30
Ile Cys Asp Gly Ile Ala Glu Ser Val Ser Arg Ala Leu Cys Lys Met
                35                  40                  45
Tyr Met Glu Lys Phe Gly Thr Ile Leu His His Asn Thr Asp Gln Val
 50                  55                  60
Glu Leu Val Gly Gly His Ala Tyr Pro Lys Phe Gly Gly Val Met
 65                  70                  75                  80
Val Ser Pro Ile Tyr Ile Leu Leu Ser Gly Arg Ala Thr Met Glu Ile
                85                  90                  95
Leu Asp Lys Glu Lys Pro Glu Val Ile Lys Leu Pro Val Gly Thr Thr
                100                 105                 110
Ala Val Lys Ala Ala Lys Glu Tyr Leu Lys Lys Val Leu Arg Asn Val
                115                 120                 125
Asp Val Asp Lys Asp Val Ile Ile Asp Cys Arg Ile Gly Gln Gly Ser
                130                 135                 140
Met Asp Leu Val Asp Val Phe Glu Arg Gln Lys Asn Glu Val Pro Leu
145                 150                 155                 160
Ala Asn Asp Thr Ser Phe Gly Val Gly Tyr Ala Pro Leu Ser Thr Thr
                165                 170                 175
Glu Arg Leu Val Leu Glu Thr Glu Arg Phe Leu Asn Ser Asp Glu Leu
                180                 185                 190
Lys Asn Glu Ile Pro Ala Val Gly Glu Asp Ile Lys Val Met Gly Leu
                195                 200                 205
Arg Glu Gly Lys Lys Ile Thr Leu Thr Ile Ala Met Ala Val Val Asp
                210                 215                 220
Arg Tyr Val Lys Asn Ile Glu Glu Tyr Lys Glu Val Ile Glu Lys Val
225                 230                 235                 240
Arg Lys Lys Val Glu Asp Leu Ala Lys Lys Ile Ala Asp Gly Tyr Glu
                245                 250                 255
Val Glu Ile His Ile Asn Thr Ala Asp Asp Tyr Glu Arg Glu Ser Val
                260                 265                 270
Tyr Leu Thr Val Thr Gly Thr Ser Ala Glu Met Gly Asp Asp Gly Ser
                275                 280                 285
Val Gly Arg Gly Asn Arg Val Asn Gly Leu Ile Thr Pro Phe Arg Pro
                290                 295                 300
Met Ser Met Glu Ala Ala Ser Gly Lys Asn Pro Val Asn His Val Gly
305                 310                 315                 320
Lys Ile Tyr Asn Ile Leu Ala Asn Leu Ile Ala Asn Asp Ile Ala Lys
                325                 330                 335
Leu Glu Gly Val Lys Glu Cys Cys Val Arg Ile Phe Ser Gln Ile Gly
                340                 345                 350
Lys Pro Ile Asn Glu Pro Lys Ala Leu Asp Ile Glu Ile Ile Thr Glu
                355                 360                 365
Asp Ser Tyr Asp Ile Lys Asp Ile Glu Pro Lys Ala Lys Glu Ile Ala
                370                 375                 380
Asn Lys Trp Leu Asp Asn Ile Met Glu Val Gln Lys Met Ile Val Glu
385                 390                 395                 400
Gly Lys Val Thr Thr Phe
                405
```

<210> SEQ ID NO 8

<211> LENGTH: 406
<212> TYPE: PRT
<213> ORGANISM: Artificial
<220> FEATURE:
<223> OTHER INFORMATION: The Asn residue at position 102 of the parent has been changed to Gln.

<400> SEQUENCE: 8

```
Met Arg Asn Ile Ile Val Lys Lys Leu Asp Val Glu Pro Ile Glu
1               5                   10                  15

Arg Pro Thr Glu Ile Val Glu Arg Lys Gly Leu Gly His Pro Asp Ser
            20                  25                  30

Ile Cys Asp Gly Ile Ala Glu Ser Val Ser Arg Ala Leu Cys Lys Met
            35                  40                  45

Tyr Met Glu Lys Phe Gly Thr Ile Leu His His Asn Thr Asp Gln Val
50                  55                  60

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Thr Met Glu Ile
                85                  90                  95

Leu Asp Lys Glu Lys Gln Glu Val Ile Lys Leu Pro Val Gly Thr Thr
            100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
            195                 200                 205

Arg Glu Gly Lys Lys Ile Thr Leu Thr Ile Ala Met Ala Val Val Asp
210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
            275                 280                 285

Val Gly Arg Gly Asn Arg Val Asn Gly Leu Ile Thr Pro Phe Arg Pro
290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
            340                 345                 350

Lys Pro Ile Asn Glu Pro Lys Ala Leu Asp Ile Glu Ile Ile Thr Glu
            355                 360                 365

Asp Ser Tyr Asp Ile Lys Asp Ile Glu Pro Lys Ala Lys Glu Ile Ala
```

-continued

```
                370                 375                 380
Asn Lys Trp Leu Asp Asn Ile Met Glu Val Gln Lys Met Ile Val Glu
385                 390                 395                 400

Gly Lys Val Thr Thr Phe
                405

<210> SEQ ID NO 9
<211> LENGTH: 406
<212> TYPE: PRT
<213> ORGANISM: Artificial
<220> FEATURE:
<223> OTHER INFORMATION: The Asn residue at position 102 of the parent
      has been changed to Thr.

<400> SEQUENCE: 9

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
                20                  25                  30

Ile Cys Asp Gly Ile Ala Glu Ser Val Ser Arg Ala Leu Cys Lys Met
            35                  40                  45

Tyr Met Glu Lys Phe Gly Thr Ile Leu His His Asn Thr Asp Gln Val
        50                  55                  60

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Thr Met Glu Ile
                85                  90                  95

Leu Asp Lys Glu Lys Thr Glu Val Ile Lys Leu Pro Val Gly Thr Thr
                100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
        130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Gly Asp Ile Lys Val Met Gly Leu
        195                 200                 205

Arg Glu Gly Lys Lys Ile Thr Leu Thr Ile Ala Met Ala Val Val Asp
210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
        275                 280                 285

Val Gly Arg Gly Asn Arg Val Asn Gly Leu Ile Thr Pro Phe Arg Pro
        290                 295                 300

Met Ser Met Glu Ala Ala Ser Gly Lys Asn Pro Val Asn His Val Gly
305                 310                 315                 320
```

```
Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
            340                 345                 350

Lys Pro Ile Asn Glu Pro Lys Ala Leu Asp Ile Glu Ile Ile Thr Glu
            355                 360                 365

Asp Ser Tyr Asp Ile Lys Asp Ile Glu Pro Lys Ala Lys Glu Ile Ala
        370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 10
<211> LENGTH: 406
<212> TYPE: PRT
<213> ORGANISM: Artificial
<220> FEATURE:
<223> OTHER INFORMATION: The Thr residue at position 93 and the Asn
      residue at position 102 of the parent have been changed to Cys and
      Ser, respectively.

<400> SEQUENCE: 10

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
            20                  25                  30

Ile Cys Asp Gly Ile Ala Glu Ser Val Ser Arg Ala Leu Cys Lys Met
        35                  40                  45

Tyr Met Glu Lys Phe Gly Thr Ile Leu His His Asn Thr Asp Gln Val
    50                  55                  60

Glu Leu Val Gly Gly His Ala Tyr Pro Lys Phe Gly Gly Val Met
65                  70                  75                  80

Val Ser Pro Ile Tyr Ile Leu Ser Gly Arg Ala Cys Met Glu Ile
                85                  90                  95

Leu Asp Lys Glu Lys Ser Glu Val Ile Lys Leu Pro Val Gly Thr Thr
            100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
        130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
    210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
```

```
                  260                 265                 270
Tyr Leu Thr Val Thr Gly Thr Ser Ala Glu Met Gly Asp Asp Gly Ser
                275                 280                 285

Val Gly Arg Gly Asn Arg Val Asn Gly Leu Ile Thr Pro Phe Arg Pro
290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
                340                 345                 350

Lys Pro Ile Asn Glu Pro Lys Ala Leu Asp Ile Glu Ile Ile Thr Glu
                355                 360                 365

Asp Ser Tyr Asp Ile Lys Asp Ile Glu Pro Lys Ala Lys Glu Ile Ala
                370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 11
<211> LENGTH: 406
<212> TYPE: PRT
<213> ORGANISM: Artificial
<220> FEATURE:
<223> OTHER INFORMATION: The Thr residue at position 93 and the Asn
      residue at position 102 of the parent have been changed to Lys and
      Ser, respectively.

<400> SEQUENCE: 11

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
                20                  25                  30

Ile Cys Asp Gly Ile Ala Glu Ser Val Ser Arg Ala Leu Cys Lys Met
                35                  40                  45

Tyr Met Glu Lys Phe Gly Thr Ile Leu His His Asn Thr Asp Gln Val
50                  55                  60

Glu Leu Val Gly Gly His Ala Tyr Pro Lys Phe Gly Gly Gly Val Met
65                  70                  75                  80

Val Ser Pro Ile Tyr Ile Leu Leu Ser Gly Arg Ala Lys Met Glu Ile
                85                  90                  95

Leu Asp Lys Glu Lys Ser Glu Val Ile Lys Leu Pro Val Gly Thr Thr
                100                 105                 110

Ala Val Lys Ala Ala Lys Glu Tyr Leu Lys Lys Val Leu Arg Asn Val
                115                 120                 125

Asp Val Asp Lys Asp Val Ile Ile Asp Cys Arg Ile Gly Gln Gly Ser
                130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
                180                 185                 190

Lys Asn Glu Ile Pro Ala Val Gly Glu Asp Ile Lys Val Met Gly Leu
                195                 200                 205
```

```
Arg Glu Gly Lys Lys Ile Thr Leu Thr Ile Ala Met Ala Val Val Asp
            210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
            245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
            275                 280                 285

Val Gly Arg Gly Asn Arg Val Asn Gly Leu Ile Thr Pro Phe Arg Pro
            290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
            325                 330                 335

Leu Glu Gly Val Lys Glu Cys Cys Val Arg Ile Phe Ser Gln Ile Gly
            340                 345                 350

Lys Pro Ile Asn Glu Pro Lys Ala Leu Asp Ile Glu Ile Ile Thr Glu
            355                 360                 365

Asp Ser Tyr Asp Ile Lys Asp Ile Glu Pro Lys Ala Lys Glu Ile Ala
            370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 12
<211> LENGTH: 406
<212> TYPE: PRT
<213> ORGANISM: Artificial
<220> FEATURE:
<223> OTHER INFORMATION: The Thr residue at position 93 and the Asn
      residue at position 102 of the parent have been changed to Arg and
      Ser, respectively.

<400> SEQUENCE: 12

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
            20                  25                  30

Ile Cys Asp Gly Ile Ala Glu Ser Val Ser Arg Ala Leu Cys Lys Met
            35                  40                  45

Tyr Met Glu Lys Phe Gly Thr Ile Leu His His Asn Thr Asp Gln Val
        50                  55                  60

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Arg Met Glu Ile
                85                  90                  95

Leu Asp Lys Glu Lys Ser Glu Val Ile Lys Leu Pro Val Gly Thr Thr
            100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
    130                 135                 140
```

```
Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
    210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
        275                 280                 285

Val Gly Arg Gly Asn Arg Val Asn Gly Leu Ile Thr Pro Phe Arg Pro
    290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
            340                 345                 350

Lys Pro Ile Asn Glu Pro Lys Ala Leu Asp Ile Glu Ile Ile Thr Glu
        355                 360                 365

Asp Ser Tyr Asp Ile Lys Asp Ile Glu Pro Lys Ala Lys Glu Ile Ala
    370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 13
<211> LENGTH: 406
<212> TYPE: PRT
<213> ORGANISM: Artificial
<220> FEATURE:
<223> OTHER INFORMATION: The Asn residue at position 102 and the Ile
      residue at position 230 have been changed to Ser and Val,
      respectively.

<400> SEQUENCE: 13

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
                20                  25                  30

Ile Cys Asp Gly Ile Ala Glu Ser Val Ser Arg Ala Leu Cys Lys Met
            35                  40                  45

Tyr Met Glu Lys Phe Gly Thr Ile Leu His His Asn Thr Asp Gln Val
        50                  55                  60

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Thr Met Glu Ile
```

-continued

```
                85                  90                  95
Leu Asp Lys Glu Lys Ser Glu Val Ile Lys Leu Pro Val Gly Thr Thr
            100                 105                 110
Ala Val Lys Ala Ala Lys Glu Tyr Leu Lys Val Leu Arg Asn Val
        115                 120                 125
Asp Val Asp Lys Asp Val Ile Ile Asp Cys Arg Ile Gly Gln Gly Ser
    130                 135                 140
Met Asp Leu Val Asp Val Phe Glu Arg Gln Lys Asn Glu Val Pro Leu
145                 150                 155                 160
Ala Asn Asp Thr Ser Phe Gly Val Gly Tyr Ala Pro Leu Ser Thr Thr
                165                 170                 175
Glu Arg Leu Val Leu Glu Thr Glu Arg Phe Leu Asn Ser Asp Glu Leu
            180                 185                 190
Lys Asn Glu Ile Pro Ala Val Gly Glu Asp Ile Lys Val Met Gly Leu
        195                 200                 205
Arg Glu Gly Lys Lys Ile Thr Leu Thr Ile Ala Met Ala Val Val Asp
    210                 215                 220
Arg Tyr Val Lys Asn Val Glu Glu Tyr Lys Glu Val Ile Glu Lys Val
225                 230                 235                 240
Arg Lys Lys Val Glu Asp Leu Ala Lys Lys Ile Ala Asp Gly Tyr Glu
                245                 250                 255
Val Glu Ile His Ile Asn Thr Ala Asp Asp Tyr Glu Arg Glu Ser Val
            260                 265                 270
Tyr Leu Thr Val Thr Gly Thr Ser Ala Glu Met Gly Asp Asp Gly Ser
        275                 280                 285
Val Gly Arg Gly Asn Arg Val Asn Gly Leu Ile Thr Pro Phe Arg Pro
    290                 295                 300
Met Ser Met Glu Ala Ala Ser Gly Lys Asn Pro Val Asn His Val Gly
305                 310                 315                 320
Lys Ile Tyr Asn Ile Leu Ala Asn Leu Ile Ala Asn Asp Ile Ala Lys
                325                 330                 335
Leu Glu Gly Val Lys Glu Cys Cys Val Arg Ile Phe Ser Gln Ile Gly
            340                 345                 350
Lys Pro Ile Asn Glu Pro Lys Ala Leu Asp Ile Glu Ile Thr Glu
        355                 360                 365
Asp Ser Tyr Asp Ile Lys Asp Ile Glu Pro Lys Ala Lys Glu Ile Ala
    370                 375                 380
Asn Lys Trp Leu Asp Asn Ile Met Glu Val Gln Lys Met Ile Val Glu
385                 390                 395                 400
Gly Lys Val Thr Thr Phe
                405
```

<210> SEQ ID NO 14
<211> LENGTH: 406
<212> TYPE: PRT
<213> ORGANISM: Artificial
<220> FEATURE:
<223> OTHER INFORMATION: The Asn residue at position 102 and the Ile
      residue at position 230 have been changed to Ser and Gly,
      respectively.

<400> SEQUENCE: 14

```
Met Arg Asn Ile Ile Val Lys Lys Leu Asp Val Glu Pro Ile Glu Glu
1               5                   10                  15
Arg Pro Thr Glu Ile Val Glu Arg Lys Gly Leu Gly His Pro Asp Ser
            20                  25                  30
```

Ile Cys Asp Gly Ile Ala Glu Ser Val Ser Arg Ala Leu Cys Lys Met
         35                  40                  45

Tyr Met Glu Lys Phe Gly Thr Ile Leu His His Asn Thr Asp Gln Val
 50                  55                  60

Glu Leu Val Gly Gly His Ala Tyr Pro Lys Phe Gly Gly Gly Val Met
 65                  70                  75                  80

Val Ser Pro Ile Tyr Ile Leu Leu Ser Gly Arg Ala Thr Met Glu Ile
                 85                  90                  95

Leu Asp Lys Glu Lys Ser Glu Val Ile Lys Leu Pro Val Gly Thr Thr
                100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
        130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
    210                 215                 220

Arg Tyr Val Lys Asn Gly Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
        275                 280                 285

Val Gly Arg Gly Asn Arg Val Asn Gly Leu Ile Thr Pro Phe Arg Pro
    290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
            340                 345                 350

Lys Pro Ile Asn Glu Pro Lys Ala Leu Asp Ile Glu Ile Ile Thr Glu
        355                 360                 365

Asp Ser Tyr Asp Ile Lys Asp Ile Glu Pro Lys Ala Lys Glu Ile Ala
    370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 15
<211> LENGTH: 406
<212> TYPE: PRT
<213> ORGANISM: Artificial
<220> FEATURE:

<223> OTHER INFORMATION: The Asn residue at position 102 and the Glu residue at position 357 of the parent have been changed to Ser and Asp, respectively.

<400> SEQUENCE: 15

```
Met Arg Asn Ile Ile Val Lys Lys Leu Asp Val Glu Pro Ile Glu Glu
 1               5                  10                  15

Arg Pro Thr Glu Ile Val Glu Arg Lys Gly Leu Gly His Pro Asp Ser
            20                  25                  30

Ile Cys Asp Gly Ile Ala Glu Ser Val Ser Arg Ala Leu Cys Lys Met
        35                  40                  45

Tyr Met Glu Lys Phe Gly Thr Ile Leu His His Asn Thr Asp Gln Val
50                  55                  60

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Thr Met Glu Ile
                85                  90                  95

Leu Asp Lys Glu Lys Ser Glu Val Ile Lys Leu Pro Val Gly Thr Thr
            100                 105                 110

Ala Val Lys Ala Ala Lys Glu Tyr Leu Lys Lys Val Leu Arg Asn Val
        115                 120                 125

Asp Val Asp Lys Asp Val Ile Ile Asp Cys Arg Ile Gly Gln Gly Ser
130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
        275                 280                 285

Val Gly Arg Gly Asn Arg Val Asn Gly Leu Ile Thr Pro Phe Arg Pro
290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
            340                 345                 350

Lys Pro Ile Asn Asp Pro Lys Ala Leu Asp Ile Glu Ile Thr Glu
        355                 360                 365

Asp Ser Tyr Asp Ile Lys Asp Ile Glu Pro Lys Ala Lys Glu Ile Ala
370                 375                 380

Asn Lys Trp Leu Asp Asn Ile Met Glu Val Gln Lys Met Ile Val Glu
```

Gly Lys Val Thr Thr Phe
            405

<210> SEQ ID NO 16
<211> LENGTH: 406
<212> TYPE: PRT
<213> ORGANISM: Artificial
<220> FEATURE:
<223> OTHER INFORMATION: The Asn residue at position 102 and the Glu
      residue at position 357 of the parent have been changed to Ser and
      Thr, respectively.

<400> SEQUENCE: 16

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
            20                  25                  30

Ile Cys Asp Gly Ile Ala Glu Ser Val Ser Arg Ala Leu Cys Lys Met
        35                  40                  45

Tyr Met Glu Lys Phe Gly Thr Ile Leu His His Asn Thr Asp Gln Val
50                  55                  60

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Thr Met Glu Ile
                85                  90                  95

Leu Asp Lys Glu Lys Ser Glu Val Ile Lys Leu Pro Val Gly Thr Thr
            100                 105                 110

Ala Val Lys Ala Ala Lys Glu Tyr Leu Lys Lys Val Leu Arg Asn Val
        115                 120                 125

Asp Val Asp Lys Asp Val Ile Ile Asp Cys Arg Ile Gly Gln Gly Ser
    130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
    210                 215                 220

Arg Tyr Val Lys Asn Ile Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
            260                 265                 270

Tyr Leu Thr Val Thr Gly Thr Ser Ala Glu Met Gly Asp Asp Gly Ser
        275                 280                 285

Val Gly Arg Gly Asn Arg Val Asn Gly Leu Ile Thr Pro Phe Arg Pro
    290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

```
Leu Glu Gly Val Lys Glu Cys Cys Val Arg Ile Phe Ser Gln Ile Gly
            340                 345                 350

Lys Pro Ile Asn Thr Pro Lys Ala Leu Asp Ile Glu Ile Ile Thr Glu
            355                 360                 365

Asp Ser Tyr Asp Ile Lys Asp Ile Glu Pro Lys Ala Lys Glu Ile Ala
            370                 375                 380

Asn Lys Trp Leu Asp Asn Ile Met Glu Val Gln Lys Met Ile Val Glu
385                 390                 395                 400

Gly Lys Val Thr Thr Phe
            405
```

<210> SEQ ID NO 17
<211> LENGTH: 406
<212> TYPE: PRT
<213> ORGANISM: Artificial
<220> FEATURE:
<223> OTHER INFORMATION: The Thr residue at position 93, the Asn residue
      at position 102 and the Ile residue at position 230 of the parent
      have been changed to Cys, Ser and Val, respectively.

<400> SEQUENCE: 17

```
Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
            20                  25                  30

Ile Cys Asp Gly Ile Ala Glu Ser Val Ser Arg Ala Leu Cys Lys Met
            35                  40                  45

Tyr Met Glu Lys Phe Gly Thr Ile Leu His His Asn Thr Asp Gln Val
    50                  55                  60

Glu Leu Val Gly Gly His Ala Tyr Pro Lys Phe Gly Gly Gly Val Met
65                  70                  75                  80

Val Ser Pro Ile Tyr Ile Leu Leu Ser Gly Arg Ala Cys Met Glu Ile
            85                  90                  95

Leu Asp Lys Glu Lys Ser Glu Val Ile Lys Leu Pro Val Gly Thr Thr
            100                 105                 110

Ala Val Lys Ala Ala Lys Glu Tyr Leu Lys Lys Val Leu Arg Asn Val
            115                 120                 125

Asp Val Asp Lys Asp Val Ile Ile Asp Cys Arg Ile Gly Gln Gly Ser
            130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
            165                 170                 175

Glu Arg Leu Val Leu Glu Thr Glu Arg Phe Leu Asn Ser Asp Glu Leu
            180                 185                 190

Lys Asn Glu Ile Pro Ala Val Gly Glu Asp Ile Lys Val Met Gly Leu
            195                 200                 205

Arg Glu Gly Lys Lys Ile Thr Leu Thr Ile Ala Met Ala Val Val Asp
            210                 215                 220

Arg Tyr Val Lys Asn Val Glu Glu Tyr Lys Glu Val Ile Glu Lys Val
225                 230                 235                 240

Arg Lys Lys Val Glu Asp Leu Ala Lys Lys Ile Ala Asp Gly Tyr Glu
            245                 250                 255

Val Glu Ile His Ile Asn Thr Ala Asp Asp Tyr Glu Arg Glu Ser Val
            260                 265                 270
```

-continued

```
Tyr Leu Thr Val Thr Gly Thr Ser Ala Glu Met Gly Asp Asp Gly Ser
        275                 280                 285

Val Gly Arg Gly Asn Arg Val Asn Gly Leu Ile Thr Pro Phe Arg Pro
        290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
            340                 345                 350

Lys Pro Ile Asn Glu Pro Lys Ala Leu Asp Ile Glu Ile Ile Thr Glu
        355                 360                 365

Asp Ser Tyr Asp Ile Lys Asp Ile Glu Pro Lys Ala Lys Glu Ile Ala
    370                 375                 380

Asn Lys Trp Leu Asp Asn Ile Met Glu Val Gln Lys Met Ile Val Glu
385                 390                 395                 400

Gly Lys Val Thr Thr Phe
                405

<210> SEQ ID NO 18
<211> LENGTH: 406
<212> TYPE: PRT
<213> ORGANISM: Artificial
<220> FEATURE:
<223> OTHER INFORMATION: The Thr residue at position 93, the Asn residue
      at position 102 and the Glu residue at position 357 of the parent
      have been changed to Cys, Ser and Asp, respectively.

<400> SEQUENCE: 18

Met Arg Asn Ile Ile Val Lys Lys Leu Asp Val Glu Pro Ile Glu Glu
1               5                   10                  15

Arg Pro Thr Glu Ile Val Glu Arg Lys Gly Leu Gly His Pro Asp Ser
            20                  25                  30

Ile Cys Asp Gly Ile Ala Glu Ser Val Ser Arg Ala Leu Cys Lys Met
        35                  40                  45

Tyr Met Glu Lys Phe Gly Thr Ile Leu His His Asn Thr Asp Gln Val
    50                  55                  60

Glu Leu Val Gly Gly His Ala Tyr Pro Lys Phe Gly Gly Val Met
65                  70                  75                  80

Val Ser Pro Ile Tyr Ile Leu Leu Ser Gly Arg Ala Cys Met Glu Ile
                85                  90                  95

Leu Asp Lys Glu Lys Ser Glu Val Ile Lys Leu Pro Val Gly Thr Thr
            100                 105                 110

Ala Val Lys Ala Ala Lys Glu Tyr Leu Lys Lys Val Leu Arg Asn Val
        115                 120                 125

Asp Val Asp Lys Asp Val Ile Ile Asp Cys Arg Ile Gly Gln Gly Ser
    130                 135                 140

Met Asp Leu Val Asp Val Phe Glu Arg Gln Lys Asn Glu Val Pro Leu
145                 150                 155                 160

Ala Asn Asp Thr Ser Phe Gly Val Gly Tyr Ala Pro Leu Ser Thr Thr
                165                 170                 175

Glu Arg Leu Val Leu Glu Thr Arg Phe Leu Asn Ser Asp Glu Leu
            180                 185                 190

Lys Asn Glu Ile Pro Ala Val Gly Glu Asp Ile Lys Val Met Gly Leu
        195                 200                 205

Arg Glu Gly Lys Lys Ile Thr Leu Thr Ile Ala Met Ala Val Val Asp
```

-continued

```
            210                 215                 220
Arg Tyr Val Lys Asn Ile Glu Glu Tyr Lys Glu Val Ile Glu Lys Val
225             230                 235                 240

Arg Lys Lys Val Glu Asp Leu Ala Lys Lys Ile Ala Asp Gly Tyr Glu
                245                 250                 255

Val Glu Ile His Ile Asn Thr Ala Asp Asp Tyr Glu Arg Glu Ser Val
                260                 265                 270

Tyr Leu Thr Val Thr Gly Thr Ser Ala Glu Met Gly Asp Asp Gly Ser
            275                 280                 285

Val Gly Arg Gly Asn Arg Val Asn Gly Leu Ile Thr Pro Phe Arg Pro
290                 295                 300

Met Ser Met Glu Ala Ala Ser Gly Lys Asn Pro Val Asn His Val Gly
305                 310                 315                 320

Lys Ile Tyr Asn Ile Leu Ala Asn Leu Ile Ala Asn Asp Ile Ala Lys
                325                 330                 335

Leu Glu Gly Val Lys Glu Cys Cys Val Arg Ile Phe Ser Gln Ile Gly
                340                 345                 350

Lys Pro Ile Asn Asp Pro Lys Ala Leu Asp Ile Glu Ile Ile Thr Glu
            355                 360                 365

Asp Ser Tyr Asp Ile Lys Asp Ile Glu Pro Lys Ala Lys Glu Ile Ala
            370                 375                 380

Asn Lys Trp Leu Asp Asn Ile Met Glu Val Gln Lys Met Ile Val Glu
385                 390                 395                 400

Gly Lys Val Thr Thr Phe
                405
```

S-ADENOSYLMETHIONINE SYNTHETASE MUTANTS, THE DNAS ENCODING THE SAME AND USES OF THE MUTANTS

FIELD OF THE INVENTION

The present invention relates to molecular biology and biotechnology field, and specifically relates to a process of generating S-adenosylmethionine synthetase mutants by using gene mutation technique, the resulting mutants and uses of the mutants.

BACKGROUND OF THE INVENTION

S-adenosylmethionine synthetase (EC 2.5.1.6) catalyzes the synthesis of S-adenosylmethionine (S-Adenosyl Methionine, SAM or SAMe) from adenosine triphosphate (ATP) and methionine. SAM exists in all biological cells. SAM has two configurations: (S,S) and (R,S), but only configuration (S,S) is biologically active. S-adenosylmethionine supplies methyl group to proteins, lipids, nucleic acids and vitamin B12 in vivo and involves in more than 100 biosyntheses and metabolic reactions in vivo in the synthesis of hormones, neurotransmitters, nucleic acids, proteins and phospholipids, and is essential for the normal function of cell membrane and human metabolism and health (Chiang P K, et al. FASEB J 1996, 10:471-480; Bottiglieri T. Am J Clin Nutr. 2002, 76:1151 S-1157S). SAM is also human body's scavenger and antidote (Mato J M. Pharmacol Ther. 1997, 73:265-280; Lu S C. Gastroenterology. 1998, 114:403-407). The amount of SAM in the body decreases as human ages. So the supplement of SAM in human is very beneficial to health. SAM is regarded as a natural food supplement in US since late 1990s.

SAM can be produced through an in vitro enzyme-catalyzed transformation process, which catalyzes the synthesis of SAM from precursor of methionine and adenosine triphosphate (ATP) using bacterium-expressed S-adenosylmethionine synthetase in vitro as described by Zhang (patent publication No: CN1483829, 2004). In the patent CN1483829, the synthesis of SAM from the precursor of methionine and adenosine triphosphate (ATP) must be conducted at 30-35° C. In addition, because the S-adenosylmethionine synthetase used is a crude extract, it contains substantive other enzymes that degrade ATP and methionine, leading to heavy consumption of expensive ATP precursors and methionine, thereby increases the cost of SAM production. Furthermore, the existence of other enzymes in the crude extract of SAM results in the presence of many contaminations in the crude product and thus increases the cost of separation and purification.

Therefore, increasing the activity of S-adenosylmethionine synthetase, shortening the reaction period and using purer S-adenosylmethionine synthetase to prevent precursor degradation are crucial to reduce the cost of SAM production.

SUMMARY OF THE INVENTION

The present invention aims to provide thermostable and highly catalytic S-adenosylmethionine synthetase mutants. Also the present invention aims to provide DNAs encoding the genes of the above described S-adenosylmethionine synthetase mutants in the present invention. Also the present invention aims to provide uses of the mutants in the in vitro synthesis of S-adenosylmethionine under higher temperature using DL-methionine and adenosine triphosphate (ATP) as substrates.

To achieve the above mentioned aims, the inventors have conducted a lot of intensive experiments. By site-directed mutagenesis on the M. jannaschii S-adenosylmethionine synthetase gene, insertion of the mutated gene into appropriate vectors after PCR amplification, then screening on MacConkey agar plates, obtained a series of S-adenosylmethionine synthetase mutants with thermostability and high catalytic activity. The mutants can efficiently catalyze the synthesis of S-adenosylmethionine under higher temperature using DL-methionine and adenosine triphosphate (ATP) as substrates.

The S-adenosylmethionine synthetase mutants obtained in this invention, characterized in that they comprise at least one mutation at positions selected from 102, 93, 230 and 357 using SEQ ID NO.: 2 in the Sequence Listing as the reference sequence and has at least 70% higher S-adenosylmethionine synthetase catalytic activity than that of wild-type using adenosine triphosphate (ATP) and methionine as substrates. In the Sequence Listing, SEQ ID NO.: 4 represents the amino acid sequence of the S-adenosylmethionine synthetase mutant in the present invention, in which Xaa represents the mutated amino acid.

Preferably, in the described wild-type sequence, asparagine (Asn) at position 102 is mutated to serine (Ser), aspartic acid (Asp), histine (His), isoleucine (Ile), proline (Pro), glutamine (Gln) or threonine (Thr); in the described wild-type sequence, threonine at position 93 is mutated to cysteine (Cys), or lysine (Lys), or arginine (Arg). In the described wildtype sequence, isoleucine at position 230 is mutated to valine (Val), or glycine (Gly); and/or in the described wild-type sequence, glutamine at position 357 is mutated to aspartate (Asp), or threonine (Thr).

These mutants have high catalytic activity. For example, in the series of mutants obtained in the present invention, a single point mutated N102S mutant has 79% higher specific activity than that of the wild type and can maintain at least 88% activity after heat treatment at 65° C. for 16 hours. Another mutant T93C with double point mutations has 262% higher specific activity than that of the wild type and can maintain at least 78.5% activity after heat treatment at 65° C. for 16 hours.

On the other hand, also the present invention provides DNAs, which comprise nucleic acid sequences encoding the S-adenosylmethionine synthetase mutants described in the invention.

On the other hand, the present invention relates to the uses of S-adenosylmethionine synthetase mutants in the synthesis of adenosylmethionine using adenosine triphosphate (ATP) and methionine as substrates. It can also be used in the synthesis of S-adenosylmethionine using L-methionine or DL-methionine and adenosine triphosphate (ATP) as substrates under higher temperature. The described adenosylmethionine can be in the form of adenosylmethionine salts such as adenosylmethionine sulfate salt, adenosylmethionine P-toluenesulfonate salt or adenosylmethionine succinic acid salt.

The described S-adenosylmethionine synthetase mutants according to this invention can be used in an impurified crude enzyme form, or in a partially purified enzyme form, or in a purified enzyme form. If necessary, the S-adenosylmethionine synthetase mutants in this invention can be prepared as immobilized enzymes, or immobilized enzymes in the form of immobilized cells using known immobilization techniques.

The mutants in the present invention have higher enzymatic activity, and reactions can proceed at higher rate even using the crude enzyme extract. Besides, the mutants can tolerate high temperature, for example, some preferably selected mutants can tolerate as high as 65° C. Therefore, after the expression in the host, heat treatment can be used to remove miscellaneous enzymes from the crude enzyme extract and S-adenosylmethionine synthetase with higher purity was obtained for the production of SAM in vitro.

Furthermore, the invented mutants can be used in industrial production of SAM under relatively high temperature such as 40-52° C. This can ensure that the mutant maintains higher activity, while shortens the reaction times so as to reduce the degradation of the substrates for the extended reaction time.

DESCRIPTION OF THE PREFERRED EMBODIMENT

Figure 1:
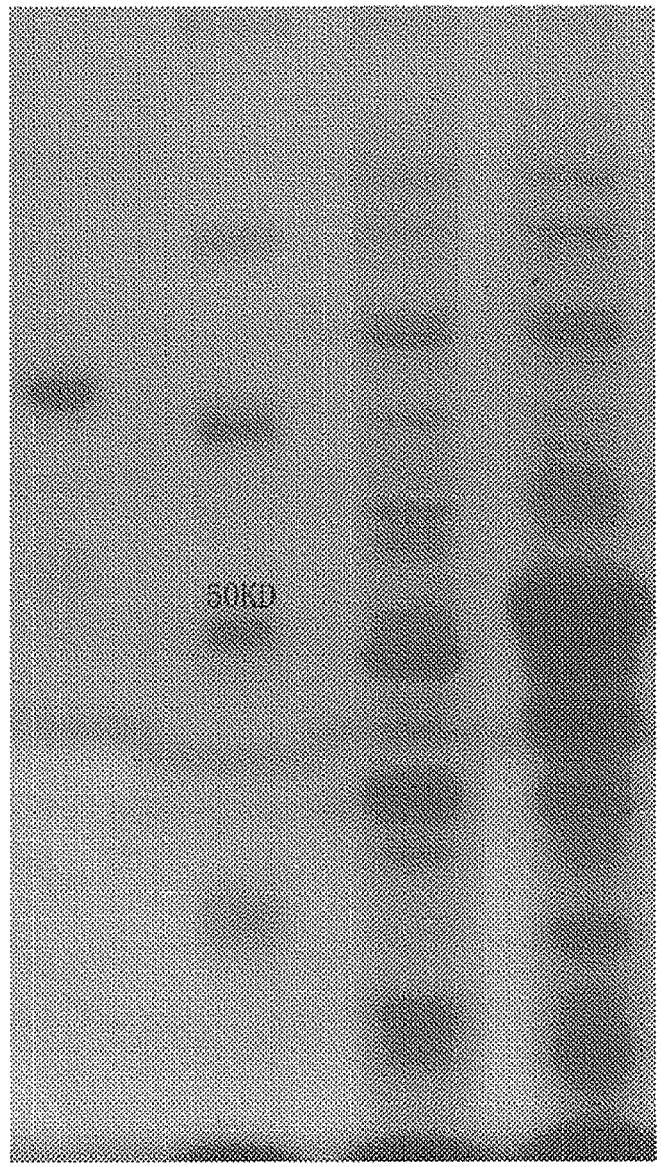
FIG. 1 shows the polyacrylamide gel electrophoresis of the wild type of S-adenosylmethionine synthetase and the mutant N102S. The four lanes starting from left to right respectively represent bovine serum albumin) protein marker, wild-type S-adenosylmethionine synthetase crude protein extract, S-adenosylmethionine synthetase mutant N102S crude protein extract (the preparation of wild type S-adenosylmethionine synthetase and mutant N102S crude protein extract is described in Examples 8-9).

Known technologies have been applied to obtain the mutants in the present invention. A plasmid carrying the wild-type S-adenosylmethionine synthetase gene was constructed first; the position of the site-directed mutagenesis and the mutant amino acids to be introduced were designed; then appropriate primers were synthesized; DNA fragments from plasmid carrying the wild-type S-adenosylmethionine synthetase gene were amplified by PCR; the DNA fragments were assembled and the full-length mutant genes were amplified by PCR; the mutant genes were cloned into appropriate vectors; the vectors containing the genes were transformed into appropriate host cells; positive clones carrying desired S-adenosylmethionine synthetase activity were screened. Plasmid DNA from positive clones were isolated and sequenced to verify the mutations. Appropriate vectors can be used in the preparations of S-adenosylmethionine synthetase mutants in the present invention. For example, suitable vectors include but not limited to, prokaryotic expression vectors pGEMT-Easy, pRSET and pES21; eukaryotic expression vectors pYD1 and pYES2/GS; cloning vectors pUC18/19 and pBluscript-SK.

In the process for preparing S-adenosylmethionine synthetase mutants in the present invention, the gene of S-adenosylmethionine synthetase mutants obtained can be expressed in prokaryotic or eukaryotic cells. Any appropriate known technologies in this field can also be used to achieve extracellular expression in prokaryotic or eukaryotic cells.

The host cells of the vectors in preparations of S-adenosylmethionine synthetase mutants in the present invention are prokaryotic or eukaryotic cells. The described prokaryotic cells include but not limited to *E. coli, Bacillus coagulans, Bacillus subtilis, M. jannaschii, Streptomyces* (e.g., *Streptomyces diastaticus* M1033); the described eukaryotic cells include but not limited to *Saccharomyces cerevisiae* and *Pichia pastoris* (e.g., *Pichia pastoris* GS115/9891).

Term "wild-type" as used herein refers to the S-adenosylmethionine synthetase (SAM) from *M. jannaschhi* (Yang's methane coccus) ATCC 43067, with its DNA sequence as SEQ ID NO.: 1 in the Sequence Listing, and with its amino acid sequence as SEQ ID NO.: 2 in the Sequence Listing. The DNA sequence of the wild-type gene in this invention is different in two nucleotides from the published DNA sequence of a *M. jannaschii* S-adenosylmethionine synthetase (Lee et al., Journal of General Microbiology, 139: 1227-1234, 1993; GenBank NC—000909); that is in comparison with the nucleic acid sequence in GenBank (GenBank NC—000909), the nucleotide of the wild-type gene in this invention is G at position 1031, corresponding to cysteine (Cys) at amino acid sequence position 344, the position 1031 of the nucleic acid sequence is A in GenBank NC—000909, corresponding to tyrosine (Tyr) at amino acid sequence position 344; the nucleotide of the wild-type gene in this invention is T at position 1044, corresponding to phenylalanine (Phe) at amino acid sequence position 348, the position 1044 of the nucleic acid sequence is A in GenBank NC—000909, corresponding to leucine (Leu) at amino acid sequence position 348.

Term "reference sequence" as used herein refers to SEQ ID NO.: 1 in the Sequence Listing when it refers a nucleic acid sequence; or SEQ ID NO.: 2 in the Sequence Listing when it refers an amino acid sequence. The alignment of the reference sequence and the sequences of the S-adenosylmethionine synthetase can be done manually or by computer (Currently there are many computer softwares available such as CLUSTALW, AMAS, DIALIGN, etc.).

"S-adenosylmethionine synthetase mutants" as used herein refers to an enzyme using SEQ ID NO.: 2 in the Sequence Listing as the reference sequence contains at least one mutation at position 102, position 93, position 230 and position 357 and has a catalytic activity at least 70% higher than that of the wild-type S-adenosylmethionine synthetase in the synthesis of S-adenosylmethionine using DL-methionine and adenosine triphosphate (ATP) as substrates. Therefore, in the present application, the variants of S-adenosylmethionine synthetase mutants including the mutants with an amino acid sequence that is the same as SEQ ID NO.: 2 in the Sequence Listing except at position 102, position 93, position 230 and position 357, such as conservative substitution, addition, or deletion of one or several amino acids, amino terminal or carboxyl terminal deletion, and partial or complete tandem repetition of SEQ ID NO.: 2, are all included in the present invention.

IUPAC nomenclature and symbolism for amino acid abbreviations are used in the present invention (*European Journal of biochemistry,* 138:9-37, 1984).

The mutants prepared according to the present invention and their properties are illustrated through specific examples below. The examples below are used to illustrate the invention only and are not intended to be regarded as the limitation of the invention. In the following examples, conventional practice or manufacturers' suggestion/protocol was followed in cases where the conditions were not specified.

Example 1

Amplification of Wild-Type Gene and Construction of pGEMT-SAM

Primers S1 and S2 (Table 1) were designed based on the sequence of GenBank NC__000909 and were used to amplify the wild-type S-adenosylmethionine synthetase gene from *M. jannaschii* ATCC 43067 (ATCC, USA).

The amplification conditions, 20 mM Tris-HCl (H 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer S1, 400 nM primer S2, 1.5 U Pfu DNA polymerase (Promega, USA), a small amount of *M. jannaschii* colony picked with an inoculating loop, and the total volume was adjusted to 50 µl with sterile distilled water.

The PCR amplification program for the reaction: 95° C., 3 min; then 40 cycles of 95° C., 50 sec, 50° C., 30 sec, 72° C., 1 min; and finally 72° C., 10 min. The amplified PCR product, about 1.3 kb in length, was digested with restriction enzymes PacI and AscI and then ligated into vector pGEMT-Easy (Promega, USA), which was digested with the same restriction enzymes PacI and AscI, to generate pGEMT-SAM. The pGEMT-SAM was sequenced to determine the DNA sequence of the wild-type S-adenosylmethionine synthetase as SEQ ID NO.:1 in the Sequence Listing and the corresponding amino acid sequence as SEQ ID NO.: 2 in the Sequence Listing.

Example 2

Site-Directed Mutagenesis of S-Adenosylmethionine Synthetase at Position 102

The site directed mutagenesis was carried out as described by Ho et al., *Gene* 77:51-59, 1989 and White et al., *PCR protocol: current methods and applications*. Totowa, N.J.: Humana Press 1993. Detailed procedures are as follows:

With pGEMT-SAM (Example 1) as template, the Asn (N) at position 102 of the wild-type amino acid sequence was mutated to Ser (S) to generate mutant N102S using primers 102SF and 102SR (Table 1).

Fragment S1SR was amplified using primer pair S1 and 102SR. Fragment SFS2 was amplified using primer pair 102SF and S2. The sequences of the primers S1 and S2 are shown in Table 1. The amplification conditions: 20 mm Tris-HCl (pH 8.8), 10 mM KCl, 10 mM (NH 4) 2 SO 4, 2 mM MgSO 4, 0.1% Triton X-100, 50 µM dATP, 50 µM dTTP, 50 µM dCTP, 50 dGTP, 1.5 U Pfu DNA polymerase (Promega, USA), 20 ng pGEMT-SAM, 400 nM primer S1 and 400 nM primer 102SR (or 400 nM primer 102SF and 400 nM primer S2), and the total volume was adjusted to 50 µl with sterile distilled water. The PCR amplification program for the reaction: 95° C., 3 min; then 35 cycles of 95° C., 50 sec, 520 C, 30 sec, 72° C., 3 min; and finally 72° C., 5 min. The PCR products, fragment S1SR and fragment SFS2, were separated on 1% agarose gel and recovered using QIAquick Gel Extraction Kit (QIAGEN, German). The full-length gene was then amplified on the following conditions: 20 mM Tris-HCl (pH 8.8), 10 mM KCl, 10 mM N14) 2 SO 4, 2 mM MgSO 4, 0.1% Triton X-100, 50 µM dATP, 50 µM dTTP, 50 µM dCTP, 50 µM dGTP, 400 nM primer S1 and 400 nM primer S2, 1.5 U Pfu DNA polymerase, 20 ng fragment S1SR and 20 ng fragment SFS2, and the total volume was adjusted to 50 µl with sterile distilled water. The PCR amplification program for the reaction: 95° C., 3 min; then 35 cycles of 95° C., 50 sec, 52° C., 30 sec, 72° C., 3 min; and finally 72° C., 5 min. The full-length mutant gene N102S was separated on 1% agarose gel and recovered using QIAquick Gel Extraction Kit. Plasmid pGEMT-N102S, generated after ligation of N102S into pGEMT-Easy, was transformed into competent cells *E. coli* HB101 (Promega, USA) and the positive clones with S-adenosylmethionine synthetase activity were screened on 1% MacConkey plates containing 10 mM adenosine triphosphate disodium, 1.0 mM L-methionine and 50 mg/L ampicillin. Plasmid pGEMT-N102S DNA was then isolated from positive clones and the introduced point mutation was confirmed correct by DNA sequencing. The amino acid sequence of N102S is shown as SEQ ID NO.: 3 in the Sequence Listing.

Mutants N1002D, N102H, N102I, N102P, N102Q and N102T were constructed following similar procedures. The primers used are shown in Table 1. The amino acid sequences of the mutants are shown as SEQ ID NOs.: 4-9 in the Sequence Listing.

Example 3

Site-Directed Mutagenesis of S-Adenosylmethionine Synthetase Mutant N102S at Position 93

The site directed mutagenesis was carried out as described by Ho et al., *Gene* 77:51-59, 1989 and White et al., *PCR protocol: current methods and applications*. Totowa, N.J.: Humana Press 1993.

With pGEMT-N102S (Example 2) as template, the Thr (T) at position 93 of the N102S was mutated to Cys (C) to generate mutant T93C using primers 93CF and 93CR (Table 1).

Fragment S1CR was amplified using primer pair S1 and 93CR. Fragment CFS2 was amplified using primer pair 93CF and S2. The sequences of the primers S1 and S2 are shown in Table 1. The amplification conditions: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer S1 and 400 nM primer 93CR or 400 nM primer 93CF and 400 nM primer S2, 1.5 U Pfu DNA polymerase (Promega, USA), 20 ng pGEMT-N102S, and the total volume was adjusted to 50 µl with sterile distilled water. The PCR amplification program for the reaction: 95° C., 3 min; then 35 cycles of 95° C., 50 sec, 52° C., 30 sec, 72° C., 3 min; and finally 72° C., 5 min. The PCR products, fragment S1CR and fragment CFS2, were separated on 1% agarose gel and recovered using QIAquick Gel Extraction Kit (QIAGEN, German). The full-length gene was then amplified on the following conditions: 20 mM Tris-HCl (pH 8.8), 10 mM KCl, 10 mM $(NH_4)_2SO_4$, 2 mM $MgSO_4$, 0.1% Triton X-100, 50 µM dATP, 50 µM dTTP, 50 µM dCTP, 50 µM dGTP, 400 nM primer S1 and 400 nM primer S2, 1.5 U Pfu DNA polymerase, 20 ng fragment S1CR and 20 ng fragment CFS2, and the total volume was adjusted to 50 µl with sterile distilled water. The PCR amplification program for the reaction: 95° C., 3 min; then 35 cycles of 95° C., 50 sec, 52° C., 30 sec, 72° C., 3 min; and finally 72° C., 5 min. The full-length mutant gene T93C was separated on 1% agarose gel and recovered using QIAquick Gel Extraction Kit. Plasmid pGEMT-T93C, generated after ligation of T93C into pGEMT-Easy, was transformed into competent cells *E. coli* HB101 and the positive clones with S-adenosylmethionine synthetase activity were screened on 1% MacConkey plates containing 10 mM adenosine triphosphate disodium, 1.0 mM L-methionine and 50 mg/L ampicillin. Plasmid pGEMT-T93C DNA was then isolated from positive clones and the introduced point mutation was confirmed correct by DNA sequencing. Mutant T93C contains N102S and T93C double mutations. The amino acid sequence of T93C is shown as SEQ ID NO.: 10 in the Sequence Listing.

Mutants T93K and T93R were constructed following similar procedures. The primers used are shown in Table 1. Mutant T93K contains N102S and T93K double mutations. Mutant T93R contains N102S and T93R double mutations. The amino acid sequences of the two mutants are shown as SEQ ID NOs.: 11-12 respectively in the Sequence Listing.

Mutants T93K and T93R were constructed following similar procedures. The primers used are shown in Table 1.

Mutant T93K contains N102S and T93K double mutations. Mutant T93R contains N102S and T93R double mutations. The amino acid sequences of the two mutants are shown as Sequences 11-12 respectively in the Sequence Listing.

Example 4

Site-Directed Mutagenesis of S-Adenosylmethionine Synthetase at Position 230

The site directed mutagenesis was carried out as described by Ho et al. *Gene* 77:51-59, 1989 and White et al., *PCR protocol: current methods and applications*. Totowa, N.J.: Humana Press 1993.

With pGEMT-N102S (Example 2) as template the Ile (I) at position 230 of the N102S was mutated to Val (V) to generate mutant I230V using primers 230VF and 230VR (Table 1).

Fragment S1VR was amplified using primer pair S1 and 230VR. Fragment VFS2 was amplified using primer pair 230VF and S2. The sequences of the primers S1 and S2 are shown in Table 1. The amplification conditions: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer S1 and 400 nM primer 230VR or 400 nM primer 230VF and 400 nM primer S2, 1.5 U Pfu DNA polymerase (Promega, USA), 20 ng pGEMT-N102S, and the total volume was adjusted to 50 μl with sterile distilled water. The PCR amplification program for the reaction: 95° C., 3 min; then 35 cycles of 95° C., 50 sec, 52° C., 30 sec, 72° C., 3 min; and finally 72° C., 5 min. The PCR products, fragment S1VR and fragment VFS2, were separated on 1% agarose gel and recovered using QIAquick Gel Extraction Kit (QIAGEN, German). The full-length gene was then amplified on the following conditions: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer S1 and 400 nM primer S2, 1.5 U Pfu DNA polymerase, 20 ng fragment S1VR and 20 ng fragment VFS2, and the total volume was adjusted to 50 μl with sterile distilled water. The PCR amplification program for the reaction: 95° C., 3 min; then 35 cycles of 95° C., 50 sec, 52° C., 30 sec, 72° C., 3 min; and finally 72° C., 5 min. The full-length mutant gene I230V was separated on 1% agarose gel and recovered using QIAquick Gel Extraction Kit. Plasmid pGEMT-I230V, generated after ligation of I230V into pGEMT-Easy, was transformed into competent cells *E. coli* HB101 and the positive clones with S-adenosylmethionine synthetase activity were screened on 1% MacConkey plates containing 10 mM adenosine triphosphate disodium, 1.0 mM L-methionine and 50 mg/L ampicillin. Plasmid pGEMT-I230V DNA was then isolated from positive clones and the introduced point mutation was confirmed correct by DNA sequencing. Mutant I230V contains N102S and I230V double mutations. The amino acid sequence of I230V is shown as SEQ ID NO.: 13 in the Sequence Listing.

Mutant I230G was constructed following similar procedures. The primers used are shown in Table 1. Mutant I230G contains N102S and I230G double mutations. The amino acid sequence of the mutant I230G is shown as SEQ ID NO.: 14 in the Sequence Listing.

Mutant I230G was constructed following similar procedures. The primers used axe shown in Table 1. Mutant I230G contains N102S and I230G double mutations. The amino acid sequence of the mutant I230G is shown as Sequence 14 in the Sequence Listing.

Example 5

Site-Directed Mutagenesis of S-Adenosylmethionine Synthetase at Position 357

The site directed mutagenesis was carried out as described by Ho et al., *Gene* 77:51-59, 1989 and White et al., *PCR protocol: current methods and applications*. Totowa, N.J.: Humana Press 1993.

With pGEMT-N102S (Example 2) as template, the Glu (E) at position 357 of the N102S was mutated to Asp (D) to generate mutant E357D using primers 357DF and 357DR (Table 1).

Fragment S1DR was amplified using primer pair S1 and 357DR. Fragment DFS2 was amplified using primer pair 357DF and S2. The sequences of the primers S1 and S2 are shown in Table 1. The amplification conditions: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer S1 and 400 nM primer 357DR or 400 nM primer 357DF and 400 nM primer S2, 1.5 U Pfu DNA polymerase (Promega, USA), 20 ng pGEMT-N102S, and the total volume was adjusted to 50 μl with sterile distilled water. The PCR amplification program for the reaction: 95° C., 3 min; then 35 cycles of 95° C., 50 sec, 52° C., 30 sec, 72° C., 3 min; and finally 72° C., 5 min. The PCR products, fragment S1DR and fragment DFS2, were separated on 1% agarose gel and recovered using QIAquick Gel Extraction Kit (QIAGEN, German). The full-length gene was then amplified on the following conditions: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer S1 and 400 nM primer S2, 1.5 U Pfu DNA polymerase, 20 ng fragment S1DR and 20 ng fragment DFS2, and the total volume was adjusted to 50 μl with sterile distilled water. The PCR amplification program for the reaction: 95° C., 3 min; then 35 cycles of 95° C., 50 sec, 52° C., 30 sec, 72° C., 3 min; and finally 72° C., 5 min. The full-length mutant gene E357D was separated on 1% agarose gel and recovered using QIAquick Gel Extraction Kit. Plasmid pGEMT-E357D, generated after ligation of E357D into pGEMT-Easy, was transformed into competent cells *E. coli* HB101 and the positive clones with S-adenosylmethionine synthetase activity were screened for on 1% MacConkey plates containing 10 mM adenosine triphosphate disodium, 1.0 mM L-methionine and 50 mg/L ampicillin Plasmid pGEMT-E357D DNA was then isolated from positive clones and the introduced point mutation was confirmed correct by DNA sequencing. Mutant E357D contains N102S and E357D double mutations. The amino acid sequence of the mutant is shown as SEQ ID NO.: 15 in the Sequence Listing.

Mutant E357T was constructed following similar procedures. The primers used are shown in Table 1. Mutant E357T contains N102S and E357T double mutations. The amino acid sequence of the mutant is shown as SEQ ID NO.: 16 in the Sequence Listing.

Mutant E357T was constructed following similar procedures. The primers used are shown in Table 1. Mutant E357T contains N102S and E357T double mutations. The amino acid sequence of the mutant is shown as Sequence 16 in the Sequence Listing.

Example 6

Construction of S-Adenosylmethionine Synthetase SAM3cv and SAM3cd with Combinations of Triple Mutations The site directed mutagenesis was carried out as described by Ho et al., *Gene* 77:51-59, 1989 and White et al., *PCR protocol: current methods and applications.* Totowa, N.J.: Humana Press 1993.

With pGEMT-T93C (Example 3) as template, the Ile (I) at position 230 of the T93C was mutated to Val (V) to generate mutant SAM3cv using primers S1 and 230VR, and 230VF and S2 (Table 1).

Fragment S1230VR was amplified using primer pair S1 and 230VR. Fragment 230VFS2 was amplified using primer pair 230VF and S2. The amplification conditions: 20 mM Tris-HCl (pH 8.8), 10 mM KCl, 10 mM $(NH_4)_2SO_4$, 2 mM $MgSO_4$, 0.1% Triton X-100, 50 μM dATP, 50 dTTP, 50 μM dCTP, 50 μM dGTP, 400 nM primer S1 and 400 nM primer 230VR or 400 nM primer 230VF and 400 nM primer S2, 1.5 U Pfu DNA polymerase (Promega, USA), 20 ng pGEMT-T93C, and the total volume was adjusted to 50 μl with sterile distilled water. The PCR amplification program for the reaction: 95° C., 3 min; then 35 cycles of 95° C., 50 sec, 52° C., 30 sec, 72° C., 3 min; and finally 72° C., 5 min. The PCR products, fragment S1230VR and fragment 230VFS2, were separated on 1% agarose gel and recovered using QIAquick Gel Extraction Kit (QIAGEN, German). The full-length gene was then amplified on the following conditions: 20 mM Tris-HCl (pH 8.8), 10 mM KCl, 10 mM $(NH_4)_2SO_4$, 2 mM $MgSO_4$, 0.1% Triton X-100, 50 μM dATP, 50 μM dTTP, 50 μM dCTP, 50 μM dGTP, 400 nM primer S1 and 400 nM primer S2, 1.5 U Pfu DNA polymerase, 20 ng fragment S1230VR and 20 ng fragment 230VFS2, and the total volume was adjusted to 50 μl with sterile distilled water. The PCR amplification program for the reaction: 95° C., 3 min; then 35 cycles of 95° C., 50 sec, 52° C., 30 sec, 72° C., 3 min; and finally 72° C., 5 min. The full-length mutant gene SAM3cv was separated on 1% agarose gel and recovered using QIAquick Gel Extraction Kit. Plasmid pGEMT-SAM3cv, generated after ligation of SAM3cv into pGEMT-Easy, was transformed into competent cells *E. coli* HB101 and the positive clones with S-adenosylmethionine synthetase activity were screened on 1% MacConkey plates containing 10 mM adenosine triphosphate disodium, 1.0 mM L-methionine and 50 mg/L ampicillin. Plasmid pGEMT-SAM3cv DNA was then isolated from positive clones and the introduced point mutation was confirmed correct by DNA sequencing. Mutant SAM3cv contains N102S, T93C and I230V triple mutations. The amino acid sequence of SAM3cv is shown as SEQ ID NO.: 17 in the Sequence Listing.

Mutant SAM3cd was constructed following similar procedures. The primers used are shown in Table 1. Mutant SAM3cd contains N102S, T93C and E357D triple mutations. The amino acid sequence of the mutant is shown as SEQ ID NO.: 18 in the Sequence Listing.

Mutant SAM3cd was constructed following similar procedures. The primers used are shown in Table 1. Mutant SAM3cd contains N102S, T93C and E357D triple mutations. The amino acid sequence of the mutant is shown as Sequence 18 in the Sequence Listing.

table 1

The Primers Used for Amplification of Wild-type
S-adenosylmethionine Synthetase and the Mutants
in Examples 2-7.

| Targeted Product | Primer Pair |
|---|---|
| Wild-Type | S1: 5' AGCCTAGGTTAATTAACTTTAAGAAGGAGATATACATATGAGA AACATAATTGTAAA 3'<br>S2: 5' ATAAGCTCAGCGGCGCGCCTTAGAATGTAGTTACTTTTCCTTCA 3' |
| Mutant N102S | 102SF: 5' AAGGAGAAAAGCGAAGTTATAAAGCTCCCAGTA 3'<br>102SR: 5' TATAACTTCGCTTTTCTCCTTATCTAAGATTTC 3' |
| Mutant N102D | 102DF: 5' AAGGAGAAAGATGAAGTTATAAAGCTCCCAGTA 3'<br>102DR: 5' TATAACTTCATCTTTCTCCTTATCTAAGATTTC3' |
| Mutant N102H | 102HF: 5' AAGGAGAAACATGAAGTTATAAAGCTCCCAGTA 3'<br>102HR: 5' TATAACTTCATGTTTCTCCTTATCTAAGATTTC3' |
| Mutant N102I | 102IF: 5' AAGGAGAAAATTGAAGTTATAAAGCTCCCAGTA 3'<br>102IR: 5' TATAACTTCAATTTTCTCCTTATCTAAGATTTC3' |
| Mutant N102P | 102PF: 5' AAGGAGAAACCGGAAGTTATAAAGCTCCCAGTA 3'<br>102PR: 5' TATAACTTCGCCTTTCTCCTTATCTAAGATTTC3' |
| Mutant N102Q | 102QF: 5' AAGGAGAAACAGGAAGTTATAAAGCTCCCAGTA 3'<br>102QR: 5' TATAACTTCCTGTTTCTCCTTATCTAAGATTTC3' |
| Mutant N102T | 102TF: 5' AAGGAGAAAACCGAAGTTATAAAGCTCCCAGTA 3'<br>102TR: 5' TATAACTTCGGTTTTCTCCTTATCTAAGATTTC3' |
| Mutant T93C | 93CF: 5' GGAAGAGCATGCATGGAAATCTTAGATAAGGA 3'<br>93CR: 5' GATTTCCATGCATGCTCTTCCAGATAATAAAAT 3' |
| Mutant T93K | 93KF: 5' GGAAGAGCAAAAATGGAAATCTTAGATAAGGA 3'<br>93KR: 5' GATTTCCATTTTTGCTCTTCCAGATAATAAAAT 3' | table 1-continued

The Primers Used for Amplification of Wild-type
S-adenosylmethionine Synthetase and the Mutants
in Examples 2-7.

| Targeted Product | Primer Pair |
|---|---|
| Mutant T93R | 93RF: 5' GGAAGAGCACGTATGGAAATCTTAGATAAGGA 3'<br>93RR: 5' GATTTCCATACGTGCTCTTCCAGATAATAAAAT 3' |
| Mutant I230V | 230VF: 5' GTTAAAAATGTGGAGGAATATAAGGAAGTTATTG 3'<br>230VR: 5' ATATTCCTCCACATTTTTAACATACCTATCAAC 3' |
| Mutant I230G | 230GF: 5' GTTAAAAATGGCGAGGAATATAAGGAAGTTATTG 3'<br>230GR: 5' ATATTCCTCGCCATTTTTAACATACCTATCAAC 3' |
| Mutant E357D | 357DF: 5' CCAATCAATGATCCAAAGGCTTTAGATATAGA 3'<br>357DR: 5' AGCCTTTGGATCATTGATTGGCTTACCAATTT 3' |
| Mutant E357T | 357TF: 5' CCAATCAATACCCCAAAGGCTTTAGATATAGA 3'<br>357TR: 5' AGCCTTTGGGGTATTGATTGGCTTACCAATTT 3' |
| Mutant SAM3cv | S1: 5' AGCCTAGGTTAATTAACTTTAAGAAGGAGATATACATATGAGA AACATAATTGTAAA 3'<br>S2: 5' ATAAGCTCAGCGGCGCGCCTTAGAATGTAGTTACTTTTCCTTCA 3'<br>230VF: 5' GTTAAAAATGTGGAGGAATATAAGGAAGTTATTG 3'<br>230VR: 5' ATATTCCTCCACATTTTTAACATACCTATCAAC 3' |
| Mutant SAM3cd | S1: 5' AGCCTAGGTTAATTAACTTTAAGAAGGAGATATACATATGAGA AACATAATTGTAAA 3'<br>S2: 5' ATAAGCTCAGCGGCGCGCCTTAGAATGTAGTTACTTTTCCTTCA 3'<br>357DF: 5' CCAATCAATGATCCAAAGGCTTTAGATATAGA 3'<br>357DR: 5' AGCCTTTGGATCATTGATTGGCTTACCAATTT 3' |

Example 7

Isolation and Purification of Wild-Type S-Adenosylmethionine Synthetase

The isolation and purification of S-adenosylmethionine synthetase were carried out essentially as described by Cabrero C, et al., Eur J Biochem. 1987, 170:299-304. Detailed procedures are as follows:

Plasmid pGEMT-SAM containing the wild-type S-adenosylmethionine synthetase gene was transformed into competent cells E. Coli HB101 and were incubated on 1% MacConkey plate containing 10 mM adenosine triphosphate disodium, 1.0 mM L-methionine and 50 mg/L ampicillin at 37° C. for 36 hours. A single colony from the plate was inoculated and cultivated in 5 ml LB supplemented with 50 mg/L ampicillin for 40 hours. The bacterial cells were pelleted, resuspended in 1 ml 100 mM Tris sodium phosphate buffer (pH 7.5), added KCl and $MgCl_2$ to final concentrations of 100 mM and 20 mM respectively, disrupted using ultrasonication and centrifuged at 17,800 g for 15 min at 10° C. to collect the supernatant as crude protein. The crude protein was heated at 65° C. for 20 min and centrifuged at 17,800 g for 15 min at 10° C. to remove the precipitate. The resultant partially purified S-adenosylmethionine synthetase was used in the subsequent enzyme activity assays and the preparation of adenosylmethionine.

Example 8

Isolation and Purification of S-Adenosylmethionine Synthetase Mutants

The isolation and purification of S-adenosylmethionine synthetase mutant N102S were carried out as described in Example 7, except the plasmid used was pGEMT-N102S. FIG. 1 shows the results of the polyacrylamide gel electrophoresis of the wild-type S-adenosylmethionine synthetase and the partially purified mutant N102S.

Example 9

Activity Assay of Wild-Type S-Adenosylmethionine Synthetase

Prepare substrate solution A containing 8 mM adenosine triphosphate disodium (ATP), 32 mM DL-methionine, 100 mM Tris hydrochloride buffer, 100 mM KCl (final concentration) and 20 mM $MgCl_2$ (final concentration) and adjusted pH to 7.5. Two hundred and fifty μl of the prepared substrate solution A was mixed with 150 μl sterile distilled water, 100 μl of the S-adenosylmethionine synthetase prepared according to Example 7, incubated at 58° C. for 20 min. The reaction was stopped by adding 300 μl 10% trichloroacetic acid (TCA), and then centrifuged at 17,800 g for 15 min at 10° C. to collect the supernatant as S-adenosylmethionine. The quantity of S-adenosylmethionine was determined by high pressure liquid chromatography (HPLC). HPLC column: C18 reverse column (Waters, USA); mobile phase: acetonitrile:water (85:15); flow rate: 0.5 mL/min; detector: ELSD 500. Injection volume was 10 μl. Protein concentration was determined using Coomassie® Plus Protein Assay Reagent Kit (Pierce, USA) and SDS-PAGE. One unit of enzyme specific activity is defined as the amount of enzyme that produces S-adenosylmethionine from 1 μmole of adenosine triphosphate (ATP) and 1 μmole of DL-methionine per min under the above described conditions. Table 2 below shows the specific activity of wild-type S-adenosylmethionine synthetase.

Example 10

Activity Assay of S-Adenosylmethionine Synthetase Mutants

The activities of S-adenosylmethionine synthetase mutants were measured as described in Example 9. Table 2 below shows the differences of the specific activities among the wild-type S-adenosylmethionine synthetase and the mutants.

TABLE 2

Differences of the Specific Activities among Wild-type S-adenosylmethionine Synthetase and the Mutants

| Enzyme | Amino Acid Sequence ID | Specific Activity |
|---|---|---|
| Wild-Type | SEQ ID NO.: 2 | 100 |
| Mutant N102S | SEQ ID NO.: 5 | 179 |
| Mutant N102D | SEQ ID NO.: 6 | 184 |
| Mutant N102H | SEQ ID NO.: 7 | 220 |
| Mutant N102I | SEQ ID NO.: 8 | 266 |
| Mutant N102P | SEQ ID NO.: 9 | 258 |
| Mutant N102Q | SEQ ID NO.: 10 | 238 |
| Mutant N102T | SEQ ID NO.: 11 | 211 |
| Mutant T93C | SEQ ID NO.: 12 | 362 |
| Mutant T93K | SEQ ID NO.: 13 | 210 |
| Mutant T93R | SEQ ID NO.: 14 | 243 |
| Mutant I230V | SEQ ID NO.: 15 | 208 |
| Mutant I230G | SEQ ID NO.: 16 | 223 |
| Mutant E357T | SEQ ID NO.: 17 | 278 |
| Mutant SAM3cv | SEQ ID NO.: 19 | 232 |
| Mutant SAM3cd | SEQ ID NO.: 20 | 232 |

Example 11

Assay of Thermostability of Wild-Type S-Adenosylmethionine Synthetase

Figure 2:
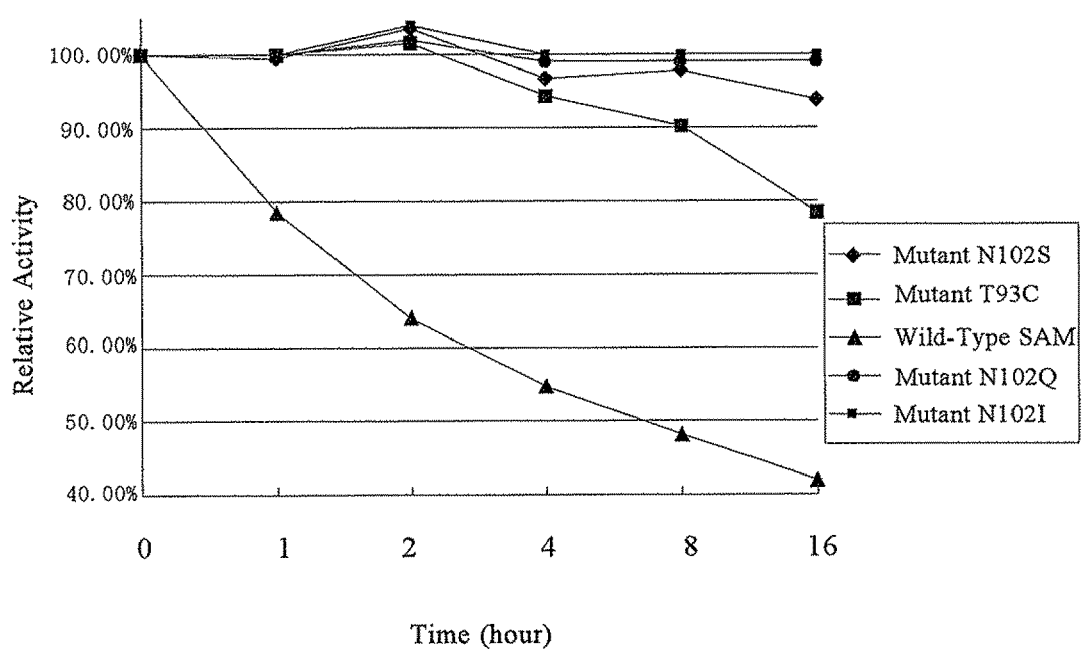
FIG. 2 shows the thermal stability of wild type S-adenosylmethionine synthetase SAM and mutants at 65° C. N102S, N102Q and N102I are S-adenosylmethionine synthetase mutants with single point mutation. T93C is S-adenosylmethionine synthetase mutant with double point mutations. Details are described in Examples 12-13.

One thousand and four hundred μl of the partially purified wild-type S-adenosylmethionine synthetase obtained according to Example 7 were added to each of seven 1.5 ml microfuge tubes, each tube contained 200 μl enzyme solution and overlaid with 200 μl mineral oil. The tubes were placed in a 65° C. water bath. One of the seven tubes was removed from the water bath at a time interval of 0 h, 0.5 h, 1 h, 2 h, 4 h, 8 h and 16 h, and centrifuged at 17,800 g for 20 min at 10° C. The specific activities of the residual S-adenosylmethionine synthetase and the residual protein in the supernatants were determined as described in Example 9. FIG. 2 shows the thermostability of wild-type S-adenosylmethionine synthetase at 65° C.

Example 12

Assay of Thermostability of S-Adenosylmethionine Synthetase Mutants

The thermostability of S-adenosylmethionine synthetase mutants N102S and T93C was measured as described in Example 11. FIG. 2 shows the thermostability of S-adenosylmethionine synthetase mutants N102S and T93C at 65° C. After heat treatment at 65° C. for 16 hours, still, the activity of the mutant N102I maintained 100% activity, mutant N102Q maintained 99% activity, mutant N102S maintained 88% activity, mutant T93C maintained 78.5% activity, while the wild-type SAM remained 41.9% activity.

This invention is not limited by the detailed description above. Various modifications can be made by those skilled in the art without departing from the scope of the invention.

The invention claimed is:

1. An isolated S-adenosylmethionine synthetase mutant, wherein said mutant comprises all of SEQ ID NO: 2 except for at least one mutation at a position selected from the group consisting of positions 102, 93, 230 and 357, wherein the mutant has S-adenosylmethionine synthetase catalytic activity of at least 70% higher than that of the S-adenosylmethionine synthetase of SEQ ID NO: 2 when using adenosine triphosphate (ATP) and methionine as substrates.

2. The S-adenosylmethionine synthetase mutant according to claim 1, wherein asparagine (Asn) at position 102 is mutated to serine (Ser), or to aspartic acid (Asp), or to histine (His), or to isoleucine (Ile), or to proline (Pro), or to glutamine (Gln), or to threonine (Thr).

3. The S-adenosylmethionine synthetase mutant according to claim 2, wherein asparagine (Asn) at position 102 is mutated to serine (Ser); and wherein the mutant further comprises a second mutation at position 93 wherein a threonine is mutated to cysteine (Cys), or to lysine (Lys), or to arginine (Arg).

4. The S-adenosylmethionine synthetase mutant according to claim 3, wherein the threonine located at position 93 is mutated to cysteine (Cys); and further comprising a third mutation at position 230 wherein an isoleucine is mutated to valine (Val).

5. The S-adenosylmethionine synthetase mutant according to claim 3, wherein the threonine located at position 93 is mutated to cysteine (Cys), and further comprising a third mutation at position 357 wherein glutamine is mutated to asparate (Asp).

6. The S-adenosylmethionine synthetase mutant according to claim 2, wherein the asparagine (Asn) located at position 102 is mutated to serine (Ser); and further comprising a second mutation at position 230 wherein an isoleucine is mutated to valine (Val) or to glycine (Gly).

7. The S-adenosylmethionine synthetase mutant according to claim 2, wherein asparagine (Asn) at position 102 is mutated to serine (Ser); and further comprising a second mutation at position 357 wherein a glutamine is mutated to asparate (Asp), or to threonine (Thr).

8. An isolated S-adenosylmethionine synthetase mutant comprising an amino acid sequence selected from the group consisting of SEQ ID NO: 3, 4, 5, 6, 7, 8, 9, 10, 11, 12, 13, 14, 15, 16, 17 and 18.

9. A method of synthesis of adenosylmethionine, said method comprising the step of combining adenosine triphosphate (ATP) and methionine with the S-adenosylmethionine synthetase mutant according to claim 1, thereby synthesizing adenosylmethionine.

10. The method according to claim 9, wherein the methionine is L-methionine.

11. The method according to claim 9, wherein the methionine is DL-methionine.

12. The method according to claim 9, wherein the adenosylmethionine is in a form of adenosylmethionine salts.

13. The method according to claim 12, wherein the adenosylmethionine salts are adenosylmethionine sulfate salts, adenosylmethionine P-toluenesulfonate salts, or adenosylmethionine succinic acid salts.

* * * * *